Figure 1:
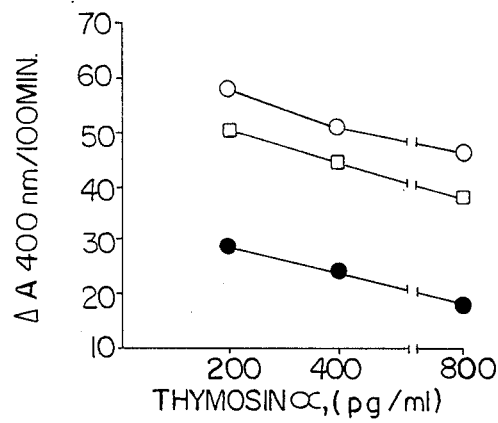

United States Patent [19]

Mutchnick et al.

[11] Patent Number: 4,950,590

[45] Date of Patent: Aug. 21, 1990

[54] METHOD AND KIT FOR ASSAY FOR MEASUREMENT OF SERUM THYMOSIN ALPHA$_1$

[75] Inventors: Milton G. Mutchnick, Ann Arbor; Frederick E. Weller, Ypsilanti, both of Mich.

[73] Assignee: Board of Governors of Wayne State University, Detroit, Mich.

[21] Appl. No.: 817,897

[22] Filed: Jan. 13, 1986

[51] Int. Cl.$^5$ ............................................. G01N 33/53
[52] U.S. Cl. ............................................ 435/7; 435/4; 436/518; 436/524; 436/528; 436/542; 436/807; 436/808; 436/809; 436/810
[58] Field of Search ............... 435/7, 4; 436/542, 518, 436/524, 528, 807-810

[56] References Cited

U.S. PATENT DOCUMENTS

| | | | |
|---|---|---|---|
| 4,055,633 | 10/1977 | Goldstein | 435/7 |
| 4,264,571 | 4/1981 | Goldstein et al. | 435/7 |
| 4,315,907 | 2/1982 | Fridlender et al. | 435/7 |
| 4,339,427 | 7/1982 | Goldstein et al. | 435/7 |
| 4,427,783 | 1/1984 | Newman et al. | 436/542 |

FOREIGN PATENT DOCUMENTS 0058428  8/1982  European Pat. Off. ............... 435/7

OTHER PUBLICATIONS

Weller et al., Journal of Immunological Methods, 80(1985), 45-53.
Parker, "The Immunoassay, Thermodynamic and Kinetic Considerations", Chapter 6, pp. 111-138, in Radioimmunoassay of Biologically Active Compounds (1976).
McClure, et al., J. of Immunology 128, 368-375, (1982).
Mutchnick et al., J. of Immunological Methods 60, 53-60 (1983).
Low, T. et al., Thymus 6, 27-42, (1984).
Naylor, et al., BioEssays 1, 63, (1984).
Goldstein, et al., Recent Prog. Horm. Res. 37, 369 (1981).
Low, et al., J. Biol. Chem. 254, 981, (1979).
Low, et al., Proc. Natl. Acad. Sci USA 78, 1162, (1981).
Low, et al., Biochem. 22, 773, (1983).
Neta, et al., Cell Immunol, 75, 173, (1983).
Svedersky, et al., Eur J. Immunol, 12, 244, (1982).
Wetzel, et al., Biochem 19, 6096, (1980).
Zatz, et al., Proc. Natl. Acad. Sci. USA 81, 2882 (1984).

Primary Examiner—Esther M. Kepplinger
Assistant Examiner—Carol A. Spiegel
Attorney, Agent, or Firm—Ian C. McLeod

[57] ABSTRACT

A micro-enzyme described immunosorbent assay (microELISA) method is described for detecting small amounts of thymosin alpha$_1$ in a solution such as serum. The method uses a known amount of an antibody to the thymosin alpha$_1$ which is reacted with the thymosin alpha$_1$ in solution to form a first complex. The solution with the first complex and unreacted antibody is then contacted with thymosin alpha$_1$ bound to a solid phase which quantitatively forms a second complex with the unreacted antibody. The amount of the second complex is determined and correlated with the amount of thymosin alpha$_1$ of the solution. Thymosin alpha$_1$ is an important hormone the presence or absence of which is significant clinically.

15 Claims, 2 Drawing Sheets

METHOD AND KIT FOR ASSAY FOR MEASUREMENT OF SERUM THYMOSIN ALPHA$_1$

BACKGROUND OF THE INVENTION (1) Field of the Invention

The present invention relates to a heterogeneous or two step assay method and test kit for quantitatively determining thymosin alpha$_1$. In particular the present invention relates to an enzyme imunossay (EIA) method for determining thymosin alpha$_1$.

(2) Prior Art

Thymosin fraction 5 (TF5) is an extract of bovine thymus containing from 40 to 50 peptide components, 20 of which have been purified to homogeneity or near homogeneity (Goldstein et al., 1981). At least 5 of these peptides (thymosin alpha$_1$, beta$_4$, beta$_9$, beta$_{10}$, and beta$_{11}$) have been sequenced, and several synthesized (Low et al., 1979, 1981, 1983; Wetzel et al., 1980). Thymosin alpha$_1$, an acidic peptide with a MW of 3108, is a potent inducer of T cells and can influence immunoregulatory T cell function (Goldstein et al., 1981). TF5 and thymosin alpha$_1$ promote the production of migration inhibitory factor in the mouse and guinea pig (Thruman et al., 1981; Neta and Salvin, 1983), the production of both alpha- and gamma-interferon in humans (Svedersky et al., 1982), and the enhancement of interleukin 2 production by human radioimmunoassay (RIA) has been developed to measure thymosin alpha$_1$ in human serum. The antiseru to thymosin alpha$_1$ was raised in rabbits against a chemically synthesized thymosin alpha$_1$, prepared by solution synthesis (Mc-Clure et al., 1982; Naylor et al., 1984).

The prior art has described a number of assay methods for determining thymosin alpha$_1$ including radio-, enzyme- and fluorescence-immunoassays. The RIA method involves the use of radioactive tracers incorporated into a modified thymosin-alpha$_1$ which competes for an antibody along with the unknown amount of thymosin-alpha$_1$ in solution. The amount of thymosin alpha$_1$ is a function of the radioactivity in the thymosin alpha$_1$ antibody complex which is isolated. The method is regarded as a homogeneous or one step method. This method is described by McClure et al in J. of Imnunology 128, 368-375 (1982), J. of Immunological Methods 60, 53-60 (1983) and in U.S. Pat. Nos. 4,264,571, 4,339,427 and 4,427,783 for instance U.S. Pat. No. 4,055,633 describes a related method. Such methods are accurate; however, the use of radioactive materials requires considerable chemical skills and also care to prevent exposure of the operator to the radioactivity. U.S. Pat. No. 4,315,907 describes a general immunoassay method.

The prior art has also described a homogeneous EIA method which uses an antibody which complexes with thymosin alpha$_1$ in solution and with solid phase bound thymosin alpha$_1$. The solid phase bound thymosin alpha$_1$ competes with the liquid phase thymosin alpha$_1$ for the antibody. The amount of thymosin alpha$_1$ in the solution is related to the solid phase bound thymosin alpha$_1$ and antibody complex formed which is measured. This method is described by Mutchnick et al in J. of Immunological Methods 60 53-60 (1983) and is referred to as an enzyme linked immunoassay (ELISA) method. It has been found that this method is not completely reliable due to variability in the complexing of the antibody to the thymosin alpha$_1$ under the conditions described in this publication.

OBJECTS

It is therefore an object of the present invention to provide an assay method for accurately determining thymosin alpha$_1$ in solution, particularly in serum. Further it is an object of the present invention to provide a test kit for practicing the method. These and other objects will become increasingly apparent by reference to the following description and the drawings.

IN THE DRAWINGS

FIG. 1 shows an optimal thymosin alpha$_1$ coating concentration. Wells were coated with three concentrations of thymosin alpha$_1$ : 100 ng/ml ( ◯ ), 50 ng/ml (□), and 10 ng/ml ( ● ). Rabbit antisera to thymosin alpha$_1$ ($2\times10^{-4}$ dilution) was added and incubated 18 hours. Goat anti-rabbit IgG (GARG) and protein A conjugated to alkaline phosphatase (AP-SA) were used, in turn, at dilutions of $10^{-3}$ and $10^{-2}$, respectively.

Figure 2:
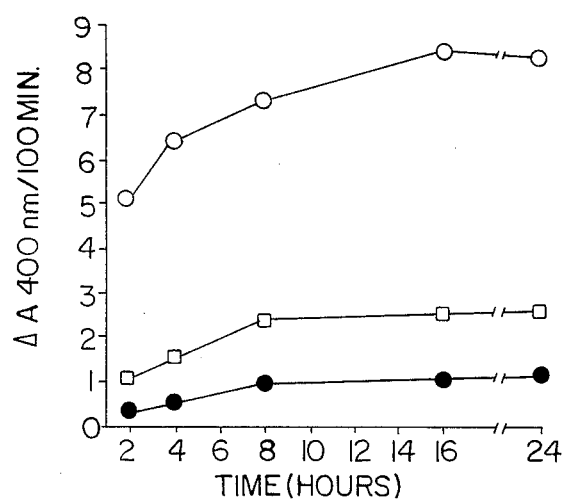

FIG. 2 shows the kinetics of the primary antibody binding. Wells were coated with 50 ng/ml thymosin alpha$_1$. Antisera to thymosin alpha$_1$ was added at dilutions of $10^{-3}$ ( ◯ ), $2\times10^{-4}$ (□) and $10^{-4}$ ( ● ) for the interval indicated. This was followed by reaction with GARG ($10^{-3}$ dilution) and then AP-SA ($2\times10^{-3}$ dilution).

Figure 3:
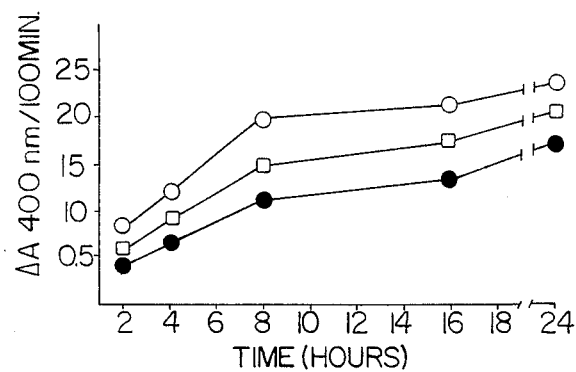

FIG. 3 shows the time development of resolution. Three concentrations of liquid phase thymosin alpha$_1$ (200 pg/ml ( ◯ ), 400 pg/ml (□), and 800 pg/ml ( ● ), containing a constant primary antibody dilution ($2\times10^{-4}$), were added and incubated for the interval indicated. The wells were then reacted, in turn, with GARG ($10^{-3}$ dilution) and AP-SA ($2\times10^{-3}$ dilution).

Figure 4:
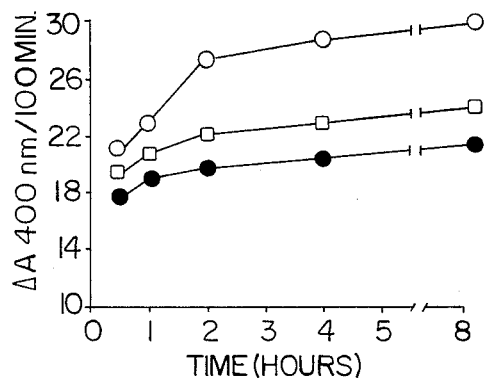

FIG. 4 shows the binding kinetics of the secondary antibody (GARG). Wells were coated with 50 ng/ml thymosin alpha$_1$, reacted with antisera to thymosin alpha$_1$ ($2\times10^{-4}$) for 18 hours. This was followed by the addition of GARG at $2\times10^{-3}$ ( ◯ ), $10^{-3}$ (□) or $5\times10^{-4}$ ( ● ) for the interval indicated with subsequent reaction using AP-SA ($2\times10^{-3}$).

Figure 5:
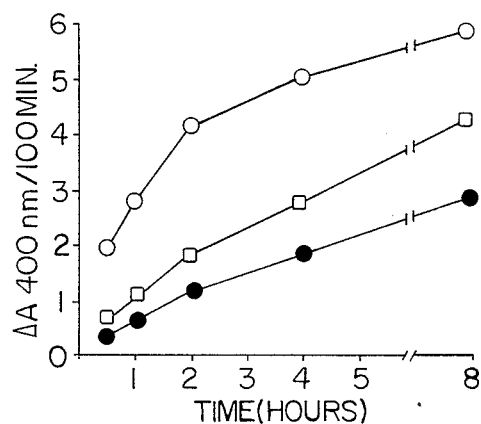

FIG. 5 shows enzyme - conjugate reaction. Wells were coated with 50 ng/ml thymosin alpha$_1$, reacted with antisera to thymosin alpha$_1$ for 18 hours. This was followed by reaction with GARG ($2\times10^{-3}$) for 2 hours. Three dilutions of AP-SA were added at $10^{-2}$ ( ◯ ), $2\times10^{-3}$ (□) and $10^{-3}$ ( ● ) for the interval indicated at room temperature.

GENERAL DESCRIPTION

The present invention relates to an assay method for detecting an amount of a specific thymic polypeptide in a solution using an antibody the improvement which comprises: reacting a specific thymic polypeptide containing solution with a known amount of a first antibody specific to binding a specific thymic polypeptide to form a first complex of the antibody with the specific thymic polypeptide which is stable without substantial disassociation wherein there is unreacted antibody remaining in the solution depending upon the amount of the specific thymic polypeptide; reacting the unreacted antibody with additional specific thymic polypeptide bound to a solid phase at a reduced temperature to form a second complex of the bound specific thymic polypeptide and antibody which is stable without substantial disassociation and discarding the solution with the first complex; and determining the amount of second complex which is inversely proportional to the specific thymic polypeptide in the solution. The preferred thymic polypeptides are the thymosins described in Thymus 6, 27–42 (1984) by Low, T. and A. Goldstein. Other thymic polypeptides are known.

The present invention further relates to an assay method for detecting an amount of thymosin alpha$_1$ in a solution using an antibody to the thymosin alpha$_1$ the improvement which comprises: reacting a thymosin alpha$_1$ containing solution with a known amount of a first antibody specific to binding pure thymosin alpha$_1$ to form a first complex of the antibody with the thymosin alpha$_1$ which is stable without substantial disassociation, wherein there is unreacted antibody remaining in the solution depending upon the amount of thymosin alpha$_1$; reacting the unreacted antibody with additional thymosin alpha$_1$ bound to a solid phase at a reduced temperature to form a second complex of the bound thymosin alpha$_1$ and antibody which is stable without substantial disassociation and discarding the solution with the first complex; and determining the amount of the second complex which is inversely proportional to the thymosin alpha$_1$ in the solution.

The present invention particularly relates to an improved micro-enzyme linked immunosorbent (Micro-ELISA) assay method for detecting an amount of thymosin-alpha$_1$ in a serum free of red blood cells by forming a complex with an antibody which comprises: reacting a serum containing thymosin alpha$_1$ with a known amount of a thymosin alpha$_1$ specific first antibody to form a thymosin alpha$_1$ and antibody first complex which is stable without substantial disassociation such that there is unbound antibody in the serum depending upon the amount of thymosin alpha$_1$ in the serum; reacting the unbound first antibody in the serum with additional thymosin alpha$_1$ bound to a solid phase to form a second complex, wherein there is unreacted bound thymosin alpha$_1$ and wherein the reaction is at a reduced temperature such that the second complex is stable without substantial disassociation and then discarding the serum with the first complex; reacting the second complex bound to the solid phase with a second antibody which reacts with the first antibody to form a third complex; reacting the third complex with an alkaline phosphatase enzyme containing protein which reacts with the second antibody to form a fourth complex; reacting the fourth complex with a compound which reacts with the enzyme as a function of time to change the optical density of a liquid substrate in contact with the enzyme and measuring the optical density of the liquid substrate at a predetermined time wherein the density is inversely proportional to the thymosin alpha$_1$ in the blood serum.

The present invention particularly relates to a kit for determining an unknown amount of thymosin alpha$_1$ by a method for detecting an amount of thymosin-alpha$_1$ in a blood serum free of red blood cells by forming a complex with an antibody which comprises: reacting the blood serum containing thymosin alpha$_1$ with a known amount of a specific first antibody to form a thymosin alpha$_1$ and antibody first complex which is stable without substantial disassociation such that there is unbound antibody depending upon the amount of thymosin alpha in the serum; reacting the unbound first antibody in the serum with additional thymosin alpha$_1$ bound to a solid phase to form a second complex, wherein there is unreacted bound thymosin alpha$_1$ and wherein the reaction is at a second reduced temperature such that the second complex is stable without substantial disassociation and discarding the serum with the first complex; reacting the second complex bound to the solid phase with a second antibody which reacts with the first antibody to form a third complex; reacting the third complex with an alkaline phosphatase protein which binds to the second antibody which reacts with the second antibody to form a fourth complex; reacting the fourth complex and determining the amount of the fourth complex in a liquid substrate after a period of time by measuring optical density which is inversely proportional to the thymosin alphaI in the blood system which comprises:

(a) substantially pure thymosin alpha$_1$;
(b) antibody to the pure thymosin alpha$_1$; and
(c) a solid substrate for the thymosin alpha$_1$;
(d) a second antibody which binds to the first antibody to form the third complex;
(e) a protein which binds to the second antibody to form the fourth complex; and
(f) a liquid substrate for determining the optical density of the fourth complex in the substrate.

The procedure as described in the examples hereinafter involves forming the first complex at 4° C. (preferably between about 0° to 15° C.) overnight (preferably 8 to 24 hours) followed by forming the second complex also at 4° C. (preferably between about 0° to 15° C.) overnight (preferably between about 8 to 24 hours). It has also been found that a reproducible curve using known concentrations for assay purposes can be obtained by forming the first complex at room temperature (preferably between about 15° to 37° C.) for 4 hours (preferably between about 2 to 8 hours) followed by forming the second complex at 4° C. (preferably between about 0° to 15° C.) overnight (preferably between about 8 to 24 hours). This latter preferred method shortens the entire assay by one day which is preferable for the development of a test kit. The second complex formation requires the reduced temperature as the critical element for obtaining a reproducible curve using known concentrations for assay purposes.

The assay method provides an accurate result by separating the first step of antibody reaction with the thymosin alpha$_1$ in solution from the second step of reacting unreacted antibody with solid phase bound thymosin. Released enzyme reacts with a chemical compound to change the optical density of a liquid substrate. The optical density measurements were then made.

SPECIFIC DESCRIPTION MATERIALS AND METHODS

Synthetic N-Ac-thymosin alpha$_1$ (lot R21-9199/002) was generously provided by Alpha 1 Biomedicals, Washington, D.C. Antiserum to thymosin alpha$_1$ was prepared as previously described (McClure et al., J. Immunol. 128, 368, 1982) and used in the non-absorbed form. Goat anti-rabbit IgG (GARG) was obtained from Kirkegaard and Perry Laboratories, Gaithersburg, MD (lot no. FA02-1). Protein A conjugated to alkaline phosphatase (AP-SA; lot no. 30109) was obtained from Zymed Laboratories, Burlingame, Calif. All antibody and antigen reagents were aliquoted in stock solutions, stored frozen and thawed once for use. Blood samples from normal adults (24–59 years of age) were allowed to coagulate for 2 hours at room temperature. The samples were centrifuged for 20 minutes and the serum stored in 1 ml aliquots at −60° C.

A stock solution of synthetic thymosin alpha$_1$ prepared in phosphate-buffered saline at a concentration suitable for the working range of the assay, i.e., 6 dose levels between 100 and 3200 pg/ml, was aliquoted, stored at −20° C. and thawed once for preparation of the standard curve. The ELISA buffer was phosphate-buffered saline: 8.0 gm NaCl, 0.2 gm KH$_2$PO$_4$, 1.15 g Na$_2$HPO$_4$ and 0.2 gm KCl to which was added 0.75 ml of Tween 20 and 0.2 g of NaN$_3$ in 1 liter of distilled water pH 7.4 (PTA). Standard solutions of synthetic thymosin alpha$_1$ (500 microl) or serum samples (250 microl) were added to 12×75 mm minisorp tubes (Nunc Immunotest tubes). PTA, 250 microl, was then added to the serum samples and 500 microl of a 1:2500 dilution of stock antiserum to thymosin alpha$_1$ was added to all tubes. The tubes were vortexed, sealed with parafilm and incubated overnight at 4° C. Wells of an Immulon 2 flat bottom microtiter plate (Dynatech Laboratories, Alexandria, Va.) were coated with synthetic thymosin alpha$_1$ by adding 200 microl/well of a 50 ng/ml thymosin alpha$_1$ solution in Dulbecco's phosphate-buffered saline (Gibco, Grand Island, N.Y.), and incubated overnight at 4° C. The plate was washed with PTA and 200 microl of each antibody-antigen solution was added from the tubes to each of 3 coated and 1 uncoated well and incubated overnight at 4° C. The plate was washed with PTA and 200 microl/well of a $2 \times 10^{-3}$ dilution of GARG (2 microl/well) was added to the plate and incubated for 2 hours at room temperature. The plate was washed with PTA and a $2 \times 10^{-3}$ dilution of AP-SA (200 microl/well) was added to the plate and incubated for 4 h at room temperature. The plate was washed with PTA and 200 microl/well of 1 mg/ml of substrate (p-nitrophenyl phosphate disodium; Sigma Chemical Co., St. Louis, Mo.) was added in carbonate-bicarbonate buffer, pH 9.8. The optical density (OD) readings were obtained at 15, 20, 25, 33$\frac{1}{3}$, 50 and 100 min using a Titertek Multiskan Spectrophotometer (Flow Laboratoraies, McLean, VA). All absorbance values reported were obtained at 400 nm and calculated to 100 min of development. Values above 1.0 were extrapolated linearly from the time at which the reading was approximately 1.0. All tests were done in triplicate with the absorbance of the uncoated well substracted from the average of the coated wells.

RESULTS

Optimal coatings with thymosin alpha$_1$

FIG. 1 shows the absorbances obtained in plates coated with 3 concentrations of thymosin alpha$_1$. In this assay a $2 \times 10^{-4}$ dilution of the primary antibody, a dilution of the enzyme conjugate were used. The plate was developed as previously described. A coating of 50 ng/ml of thymosin alpha$_1$ was used in the subsequent experiments.

Primary antibody binding

The rate at which the primary antibody binds to the coating in the wells and the effect of concentration on the kinetics is shown in FIG. 2. Three dilutions of primary antibody were used ($10^{-3}$, $2 \times 10^{-4}$ and $10^{-4}$). The reaction was complete by 8 h with little change in reactivity at 16 h and 24 h. FIG. 3 shows the resolution between 3 points on the standard curve over the same length of time using the $2 \times 10^{-4}$ dilution of primary antibody The plates were coated as described, the liquid phase primary antibody-antigen added and allowed to incubate for 2, 4, 8, 16 and 24 h at 4° C. The secondary antibody was added at a $10^{-3}$ dilution and enzyme conjugate at a $2 \times 10^{-3}$ dilution. The plate was developed as described. Maximum binding of the primary antibody to the antigen was achieved after 24 h of incubation. A $2 \times 10^{-4}$ dilution of the primary antibody resulted in the most consistent binding and resolution over the required range of the curve.

Secondary antibody binding

FIG. 4 shows the rate of binding of the secondary antibody to the primary antibody, and the effect of concentration on the kinetics. The plates were coated as described, then a $2 \times 10^{-4}$ dilution of primary antibody was added for 18 h. Three dilutions of the secondary antibody were added ($2 \times 10^{-3}$, $10^{-3}$, $5 \times 10^{-4}$) and allowed to incubate for $\frac{1}{2}$, 1, 2, 4, and 8 h at room temperature. Enzyme conjugate ($2 \times 10^{-3}$) was added for 4 h and the plates developed. The reaction was complete at 2 h with little change observed when the reaction was extended to 8 h.

Enzyme conjugate binding

The rate of binding of the enzyme conjugate to the primary-secondary antibody complex is shown in FIG. 5. Three dilutions of enzyme conjugate were used ($10^{-2}$, $2 \times 10^{-3}$, $10^{-3}$) to determine the effect of concentration on kinetics. Plates were prepared with coating, primary antibody and secondary antibody as described, then enzyme conjugate was added and allowed to incubate $\frac{1}{2}$, 1, 2, 4 and 8 h at room temperature. An incubation time of 4 h and a $2 \times 10^{-3}$ dilution of the conjugate were selected to minimize background in OD readings. The substrate reacts with the enzyme to produce a yellow color which is measured by the optical density readings.

Dose-response of the Synthetic Standard and Human Serum

Synthetic thymosin alpha$_1$ produced a dose-response relationship as shown in Table I. The ELISA exhibited the characteristics of having a minimal detectable dose (Beta$_i$/Beta$_o \times 100=90$) of 100 pg/ml. Standard curves in 10 experiments yielded a mean slope of $-0.971 \pm 0.079$ (SD) and a useful operating range between 100 and 1600 pg/ml. Regression analysis of the concentration of synthetic thymosin alpha$_1$ vs. absorbance showed an r value of $-0.992 \pm 0.005$. The variation within assays averaged 4.7% between assays 9.3%.

TABLE I

STANDARD DOSE-RESPONSE CURVE FOR SYNTHETIC THYMOSIN ALPHA$_1$

| [Thymosin alpha$_1$][a] | Within-assay variation | | | Between-assay variation | | |
|---|---|---|---|---|---|---|
| | n | Mean ± SE[b] | % CV[c] | n | Mean ± SD | % CV |
| 0 | 6 | 3.111 ± 0.112 | 3.6 | 9 | 3.119 ± 0.248 | 7.9 |
| 100 pg/ml | 6 | 2.687 ± 0.120 | 4.3 | 9 | 2.787 ± 0.199 | 6.8 |
| 200 pg/ml | 6 | 2.489 ± 0.090 | 3.5 | 9 | 2.552 ± 0.188 | 7.2 |
| 400 pg/ml | 6 | 2.141 ± 0.052 | 2.4 | 9 | 2.205 ± 0.180 | 8.1 |
| 800 pg/ml | 6 | 1.836 ± 0.083 | 4.5 | 9 | 1.796 ± 0.179 | 9.9 |
| 1600 pg/ml | 6 | 1.647 ± 0.061 | 3.7 | 9 | 1.603 ± 0.171 | 10.7 |
| 3200 pg/ml | 6 | 1.310 ± 0.137 | 10.5 | 9 | 1.301 ± 0.204 | 14.9 |

[a]PTA containing increasing concentrations of liquid-phase thymosin alpha$_1$ and a constant dilution of antiserum to thymosin alpha$_1$ ($2 \times 10^{-4}$) was allowed to react in wells for 18 hours at 4° C.
[b]Absorbance at 400 nm after reaction for 100 min.
[c]% CV, percentage coefficient of variance.

The mean slope obtained using serial dilutions of 10 human serum samples was $-0.894 \pm 0.096$ with a mean r value of $-0.984 \pm 0.021$ indicating a response for serum thymosin alpha$_1$ nearly equal and parallel to that given by the synthetic peptide standard. Background was minimal (<10% of OD reading) and did not fluctuate proportionally with serial dilution. A 1:4 dilution of serum was established as the most accurate, based on weighted averaging of serial dilution measurements and minimum variability.

Specificity of the ELISA

The specificity of the ELISA was determined by assaying preparations of thymosin alpha$_1$, thymic humoral factor (THF); insulin, glycagon and somatostatin as shown in Table II. Increasing amounts of each preparation were added to the ELISA system until levels were reached which were well above the known physiological concentrations in serum or until a practical limit was reached. For those preparations which did not produce a response significantly different from the zero dose level (>10% inhibition or Beta$_i$/Beta$_o$=0.90), the largest dose tested is indicated. It was possible to produce at least a 10% inhibition with some unrelated hormones when large amounts were added, but the dose levels required to produce a response in the thymosin alpha$_1$ ELISA were well above the known concentrations of those hormones in human blood. There appeared to be no significant antigenic similarity between thymosin alpha and THF.

TABLE II

SPECIFICITY OF ELISA FOR THYMOSIN ALPHA$_1$

| [Thymosin alpha$_1$][b] pg/ml | % <OD[c] | Liquid-phase concentration of antigen/ml[a] | | | | |
|---|---|---|---|---|---|---|
| | | Concentration | Insulin % <OD | Glucagon % <OD | THF[d] % <OD | Somatostatin % <OD |
| 100 | −10.6 | 100 pg/ml | −4.5 | −5.5 | −1.6 | −1.5 |
| 200 | −18.2 | 500 pg/ml | −2.4 | −5.2 | −2.1 | −1.8 |
| 400 | −29.3 | 1 ng/ml | −2.3 | −7.1 | −2.7 | −1.7 |
| 800 | −42.4 | 5 ng/ml | −7.6 | −4.7 | −1.7 | −2.7 |
| 1600 | −48.6 | 10 ng/ml | −7.7 | −5.3 | −0.2 | −4.6 |
| 3200 | −58.0 | 100 ng/ml | −7.1 | −5.6 | −7.7 | ND |
| ND[e] | ND | 500 ng/ml | −12.9 | −3.0 | −26.5 | ND |

[a]PTA containing increasing concentrations of test antigens and a constant dilution of antisera to thymosin alpha$_1$ ($2 \times 10^{-4}$) was allowed to react in wells for 18 h at 4° C.
[b]PTA containing increasing concentrations of thymosin alpha$_1$ and a constant dilution of antisera to thymosin alpha$_1$ ($2 \times 10^{-4}$) was allowed to react in wells for 18 h at 4° C.
[c]% <OD represents the percentage decrease in the absorbance reading between the value obtained with no antigen in the liquid phase and the value obtained with each respective amount of antigen in the liquid phase.
[d]THF, thymic humoral factor.
[e]ND, not done.

Precision of Measurements of Serum Thymosin alpha$_1$

A recovery experiment was used to indicate the validity of the measurements of thymosin alpha$_1$ in serum. Exogenous synthetic thymosin alpha$_1$ was added in increasing doses to a series of tubes containing a constant volume of human serum. A control serum sample which contained $836 \pm 253$ pg/ml was chosen for the experiment shown in Table III.

TABLE III

RECOVERY EXPERIMENT FOR MEASUREMENT OF EXOGENOUS SYNTHETIC THYMOSIN alpha$_1$ ADDED TO SERUM

| Thymosin alpha$_1$ in serum | Synthetic thymosin alpha$_1$ added(pg/ml) | Expected pg/ml | Measured pg/ml | % of expected |
|---|---|---|---|---|
| 836 | 500 | 1336 | 1120 | 84 |
| 836 | 1000 | 1836 | 1720 | 94 |
| 836 | 2000 | 2836 | 3160 | 111 |
| 836 | 3000 | 3836 | 3880 | 101 |
| 836 | 4000 | 4836 | 5400 | 112 |
| 836 | 5000 | 5836 | 6200 | 106 |
| 836 | 6000 | 6836 | 6800 | 99 |

The doses of exogenously added synthetic thymosin alpha$_1$ ranged from 500 pg/ml to 6000 pg/ml and the recoveries varied from 84% to 112%. Recoveries of nearly 100% of the amount of the added peptide indicated a lack of significant interference by constituents contained in the serum. Table IV shows the within-assay and between-assay variation obtained on 3 different serum samples. These serum samples varied in thymosin alpha$_1$ content from a low of 836 pg/ml to a high of 2016 pg/ml. The percent variance for determinations within an assay was between 10 and 22%, while the between assay variance ranged from 25 to 30%. The data for between assay variance was collected over a 3 month period.

TABLE IV

PRECISION OF MEASUREMENTS OF SERUM THYMOSIN ALPHA$_1$

| Serum Sample | Within-assay Variation | | | Between-assay Variation | | |
|---|---|---|---|---|---|---|
| | n | Mean ± 1 SD | % CV[a] | n | Mean ± 1 SD | % CV |
| Sample A | 12 | 887 ± 114 | 12.9 | 10 | 836 ± 253 | 30.3 |
| Sample B | 6 | 1167 ± 252 | 21.6 | 6 | 1340 ± 407 | 30.4 |
| Sample C | 6 | 2016 ± 264 | 13.1 | 6 | 1692 ± 417 | 24.6 |

[a]% CV, percentage coefficient of variance

Comparison of the ELISA and RIA

Since the RIA for thymosin alpha$_1$ was developed and established as the method for measuring thymosin alpha$_1$, we compared values obtained using the ELISA to those of the RIA. Serum samples from 30 individuals were assayed using the ELISA. We obtained a mean value of $871 \pm 439$ pg/ml of thymosin alpha$_1$. In an unpaired comparison, 30 serum samples collected in identical fashion from a different group of 30 normal controls were measured using the RIA (Naylor et al., 1984). A mean value of 651±524 pg/ml was obtained and was not significantly different from the value using the ELISA. In a paired comparison, the thymosin alpha$_1$ levels in 15 serum samples were measured using the ELISA and the same 15 samples were measured using the RIA. The ELISA gave a mean value of 851±515 pg/ml while the RIA gave a mean value of 641±415 pg/ml. The paired t-test value of 1.282 did not indicate a significant difference at the 95% confidence level.

Discussion

The development of the ELISA was made possible by the binding affinity and stability of the antibody-antigen complex at 4° C. (McClure et al., J. Immunol. 128, 368, 1982). In a previously developed ELISA for thymosin alpha$_1$ (Mutchnick et al., J. Immunol. Methods 60,53, 1983) we used the primary antibody-antigen disassociation characteristic at room temperature to establish a standard curve. When the disassociation microELISA method was applied to measurement of serum thymosin alpha$_1$, unacceptable within- and between-assay variation was encountered. During the development of the previous ELISA, the affinity and stability of the antibody-antigen complex at 4° C. was again observed. This made possible the development of the current more accurate and reproducible assay.

The ELISA for thymosin alpha$_1$ was developed as an alternative to the RIA. Although the concentrations of thymosin alpha$_1$, its antisera, and the methodology are unique to this assay, its accuracy and reproducibility show remarkable similarities to the RIA. Since the primary antibody in the ELISA is identical to the antibody used in the RIA (McClure et al., 1982), evaluation of specificity using additional hormones, peptides and proteins was not undertaken. The synthetic thymosin alpha$_1$ standard produced a dose response which was linear and useful for quantitation from 100 to 1600 pg/ml. Since a 1:4 dilution of an unknown serum sample is used for measurement, the standard working range of the assay is from 400 to 6400 pg/ml in the undiluted sample. The measurement of serum levels of thymosin alpha$_1$ shows greater variability than that obtained with the synthetic standard since the serum is diluted 1:4.

Although the 48 hr time frame for accomplishing the ELISA is similar to the RIA, no isotopes are utilized and the synthetic analogue of the naturally occurring thymosin alpha$_1$ (N-Ac-(Tyr$^1$) thymosin alpha$_1$ ) is not required. The microELISA represents an alternative method for determining serum thymosin alpha$_1$ levels. Protein A can be derived from a microorganism, particularly *Staphylococcus aureus*.

The first antibody can be produced by vaccinating a mammal with pure thymosin alpha$_1$ produced by chemical synthesis and collecting and isolating the first antibody from blood serum of the mammal. The bound thymosin alpha$_1$ can be produced by chemical synthesis and is substantially pure. The first antibody preferably is isolated from rabbit as the mammal blood serum and the second antibody is an antirabbit IgG reactive with the first antibody. The protein can be protein A derived from a microorganism bound to an alkaline phosphatase enzyme. Controls with first antibody reacted with the solid phase without thymosin alpha$_1$ can be determined and a difference in optical density determined between the solid phase with and without thymosin alpha$_1$.

We claim:

1. In an assay method for detecting an amount of a specific thymic polypeptide in a solution from body fluids using an antibody the improvement which comprises:
  (a) reacting a specific thymic polypeptide containing solution from body fluids which is free of cells with a known amount of a first antibody specific to binding said thymic polypeptide, wherein the specific thymic polypeptide is selected from the group consisting of thymosin alpha$_1$, thymosin beta$_4$, thymosin beta$_9$, thymosin beta$_{10}$ and thymosin beta11 to form a first complex of the antibody with the specific thymic polypeptide at a temperature between about 0° to 37° C. wherein there is unreacted antibody remaining in the solution in an amount depending upon the amount of the specific thymic polypeptide;
  (b) reacting the unreacted antibody with an additional amount of the specific thymic polypeptide bound to a solid phase at a temperature between about 0° to 15° C. to form a second complex of the specific bound thymic polypeptide and antibody and discarding the solution with the first complex; and
  (c) determining the amount of second complex which is inversely proportional to the specific thymic polypeptide in the solution.

2. In a assay method for detecting an amount of thymosin alpha$_1$ in a solution from the body using an antibody the improvement which comprises:
  (a) reacting a thymosin alpha$_1$ containing solution from the body which is free of cells with a known amount of a first antibody specific to binding pure thymosin alphaI to form a first complex of the antibody with thymosin alphaI at a temperature between about 0° C. and 37° C. wherein there is unreacted antibody remaining in the solution in an amount depending upon the amount of thymosin alpha$_1$;
  (b) reacting the unreacted antibody with an additional amount of the thymosin alpha$_1$ bound to a solid phase at a temperature between about 0° C. and 15° C. to form a second complex of the bound thymosin alphaI and antibody and discarding the solution with the first complex; and
  (c) determining the amount of second complex which is inversely proportional to the thymosin alpha$_1$ in the solution.

3. The method of claim 2 wherein the second complex bound to the solid phase is radioactive and wherein the determination of the amount of the thymosin alpha$_1$ in solution is based upon the radioactivity of the second complex.

4. The method of claim 2 wherein the amount of the second complex is determined by incorporating a fluorescent or an enzyme and reactive substrate label into the second complex which is measured and related to an amount of the thymosin alpha$_1$ in solution.

5. In a micro-enzyme linked immunosorbent assay method for detecting an amount of thymosin-alpha$_1$ in a serum free of red blood cells by forming a complex with an antibody the improvement which comprises:
  (a) reacting a serum containing thymosin alpha$_1$ with a known amount of a specific first antibody to form a thymosin alpha$_1$ and antibody first complex at a temperature between about 0° and 37° C. such that there is unbound antibody in the serum in an amount depending upon the amount of thymosin alpha$_1$ in the serum;

(b) reacting the unbound first antibody in the serum with an additional amount of the thymosin alpha$_1$ bound to a solid phase to form a second complex, wherein there is unreacted bound thymosin alpha$_1$ and wherein the reaction is at a temperature between about 0° and 15° C. and then discarding the serum with the first complex;

(c) reacting the second complex bound to the solid phase with a second antibody which reacts with the first antibody to form a third complex;

(d) reacting the third complex with an alkaline phosphatase enzyme containing protein which reacts with the second antibody to form a fourth complex;

(e) reacting the fourth complex with a liquid substrate which reacts with the enzyme as a function of time to change the optical density of the liquid substrate and measuring the optical density of the liquid substrate as an indication of the thymosin alpha$_1$ present in the serum wherein the optical density is inversely proportional to the thymosin alpha$_1$ in the serum.

6. The method of claim 5 wherein the first antibody is produced by vaccinating a mammal with substantially pure thymosin alpha$_1$ produced by chemical synthesis and collecting and isolating the first antibody from blood serum of the mammal.

7. The method of claim 5 wherein the bound thymosin alpha$_1$ is produced by chemical synthesis and is substantially pure.

8. The method of claim 5 wherein the first complex is formed by reacting the thymosin alpha$_1$ with the antibody at 15° to 37° C. for 2 to 8 hours and then reducing the temperature to 0° to 15° C. for 8 to 24 hours and wherein the second complex is formed at 0° to 15° C.

9. The method of claim 5 wherein the first complex is formed by reacting the thymosin alpha$_1$ with the antibody at 0° to 15° C. for 8 to 24 hours and then forming the second complex at 4° C. for 8 to 24 hours.

10. The method of claim 5 wherein the first antibody is isolated from a rabbit as the mammal blood serum and wherein the second antibody is antirabbit IgG.

11. The method of claim 5 wherein the protein is protein A which is derived from a microorganism.

12. The method of claim 11 wherein the protein A is derived from *Staphylococcus aureus*.

13. The method of claim 5 wherein the liquid substrate is disodium p-nitrophenyl phosphates and wherein the enzyme is conjugated to Protein A which is reacted with the third complex to form the fourth complex.

14. The method of claim 5 wherein, in addition, controls with the first antibody reaction with the solid phase without thymosin alpha$_1$ are determined and wherein a difference in optical density is determined between the solid phase with and without the solid bound thymosin alpha$_1$.

15. The method of claim 5 wherein the first antibody is produced by vaccinating a mammal with pure thymosin alpha$_1$ produced by chemical synthesis and collecting and isolating the first antibody from blood serum of the mammal; wherein the bound thymosin alpha$_1$ is produced by chemical synthesis and is substantially pure; wherein the first antibody is isolated from rabbit as the mammal blood serum and the second antibody is an antirabbit IgG reactive with the first antibody; wherein the protein is protein A derived from a microorganism bound to an alkaline phosphatase enzyme; and wherein in addition controls with first antibody reacted with the solid phase without thymosin alpha$_1$ are determined and wherein a difference in optical density is determined between the solid phase with and without thymosin alpha$_1$.

* * * * *

UNITED STATES PATENT AND TRADEMARK OFFICE
CERTIFICATE OF CORRECTION

PATENT NO. : 4,950,590
DATED : 1990 August 21
INVENTOR(S) : Milton G. Mutchnick and Frederick E. Weller It is certified that error appears in the above—identified patent and that said Letters Patent is hereby corrected as shown below:

Column 1, line 26 "Thruman" should be --Thurman--.

Column 1, line 29, after "human" the following should be inserted --lymphocytes (Zatz et al., 1984). A sensitive and specific--.

Column 1, line 31 "antiseru" should be --antiserum--.

Column 1, line 48, after "instance" a period --.-- should be inserted.

Column 3, line 63 "alpha" should be --alpha$_1$--.

Column 4, line 12, "alphaI" should be --alpha$_1$--.

Column 5, line 52, before "dilution" the following should be inserted --10$^{-3}$ dilution of the secondary antibody and a 10$^{-2}$--.

Column 5, line 66, after "antibody", a period --.-- should be inserted.

Column 7, line 15 "glycagon" should be --glucagon--.

Column 7, line 40 "alpha" should be --alpha$_1$--.

Column 10, line 9 (Claim 1), "poIypeptide" should be --polypeptide--.

Column 10, line 12 (Claim 1) "beta11" should be -beta$_{11}$--.

UNITED STATES PATENT AND TRADEMARK OFFICE
CERTIFICATE OF CORRECTION

PATENT NO. : 4,950,590

DATED : 1990 August 21

INVENTOR(S) : Milton G. Mutchnick and Frederick E. Weller

It is certified that error appears in the above-identified patent and that said Letters Patent is hereby corrected as shown below:

Column 10, lines 35 and 36 (Claim 2) "alphaI" should be --alpha$_1$--.

Column 10, line 45 (Claim 2) "alphaI" should be --alpha$_1$--.

Column 12, line 13 (Claim 13) "phosphates" should be --phosphate--.

Signed and Sealed this

Third Day of March, 1992

Attest:

*Attesting Officer*

HARRY F. MANBECK, JR.

*Commissioner of Patents and Trademarks*